United States Patent [19]

Shuler

[11] Patent Number: 4,923,441
[45] Date of Patent: May 8, 1990

[54] SURGICAL CUTTING INSTRUMENT WITH TITANIUM NITRIDE COATING ON AN INNER TUBULAR MEMBER

[75] Inventor: Donald K. Shuler, Largo, Fla.
[73] Assignee: Concept, Inc., Largo, Fla.
[21] Appl. No.: 314,196
[22] Filed: Feb. 23, 1989
[51] Int. Cl.⁵ .............................................. A61B 17/32
[52] U.S. Cl. ...................................... 604/22; 606/170
[58] Field of Search ............ 128/305, 303 R; 604/22; 384/280, 317, 476, 900, 912, 913; 408/144; 427/190; 606/168, 170, 171

[56] References Cited

U.S. PATENT DOCUMENTS

| | | |
|---|---|---|
| 3,941,903 | 3/1976 | Tucker, Jr. ......................... 427/190 |
| 4,681,541 | 7/1987 | Snaper ................................ 408/144 |
| 4,811,734 | 3/1989 | McGurk-Burleson et al. ..... 128/305 |

OTHER PUBLICATIONS

"Wear Resistant Materials and Coatings", Lillian Ng and Yngve Naerheim.
Balzers Bulletins 120, 140, 150 and 210.
Balzers Bulletin 180: Substrate Material Guide.
Balzers Bulletin 130: Questions & Answers.
Balzers Bulletin No. 200 TIN Coating: An Option for Superior.
Tool Performance.
Balzers brochure jacket "Balzers Titanium Nitride Coating For Industry".

Primary Examiner—Michael H. Thaler
Assistant Examiner—William Lewis
Attorney, Agent, or Firm—Epstein, Edell & Retzer

[57] ABSTRACT

A surgical cutting instrument having elongate inner and outer tubular members with distal ends cooperating to cut bodily tissue and aspirate the cut bodily tissue through the inner tubular member includes a coating of titanium nitride formed on the inner tubular member by physical vapor deposition to extend from the distal end of the inner tubular member to the proximal end of the inner tubular member such that the titanium nitride coating forms an elongate bearing surface extending along the length of the surgical cutting instrument preventing cocking or skewing of the inner tubular member relative to the outer tubular member while also preventing galling and possible seizure by distributing or dispersing heat along the surgical cutting instrument.

6 Claims, 1 Drawing Sheet

4,923,441 and manufacturing techniques and results in a relatively expensive product that cannot be feasibly supplied for single patient use, i.e., be disposable. Additionally, such bearing structures present increased opportunities for malfunction due to sticking and obstruction. Another manner in which to precisely position and align the inner member is to make the outer diameter of the inner member substantially the same as the inner diameter of the outer tubular member; however, since it is preferred to construct the inner tubular member and the outer tubular member of stainless steel and since stainless steel is relatively soft and does not serve well as a bearing surface, this approach has had the disadvantage of causing galling and subsequent seizure. That is, as the stainless steel surfaces of the inner and outer tubular members bear on each other, heat is generated from friction and causes thermal expansion creating greater friction and a concomitant increase in heat eventually causing the grain structure of the stainless steel tubular members to "flake" in turn increasing temperature due to abrasion until the instrument seizes. No adequate solution to this problem has been found prior to the present invention, it being noted that biocombatibility must be considered in using a lubricant coating between the inner and outer members.

SURGICAL CUTTING INSTRUMENT WITH TITANIUM NITRIDE COATING ON AN INNER TUBULAR MEMBER

BACKGROUND OF THE INVENTION

1. Field of the Invention

The present invention pertains to surgical cutting instruments and, more particularly, to surgical cutting instruments having elongate, inner and outer tubular members with distal ends cooperating to cut or resect bodily tissue, the cut tissue being aspirated through the inner member.

2. Discussion of the Prior Art

The use of elongate surgical cutting instruments has become well accepted in performing closed surgery, such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery conventionally have an elongate outer tubular member terminating at a distal end having an opening in the side wall, the end wall or both to form a cutting port or window and an elongate inner tubular member concentrically disposed in the outer tubular member and having a distal end disposed adjacent the opening in the distal end of the outer tubular member. The distal end of the inner tubular member has a surface or edge for engaging tissue via the opening in the distal end of the outer tubular member and in many cases cooperates with the opening to shear or cut tissue. The inner tubular member is rotatably driven at its proximal end, normally via a handpiece having a small electric motor therein controlled by finger-actuated switches on the handpiece, a foot switch or switches on a console supplying power to the handpiece. The distal end of the inner tubular member can have various configurations dependent upon the surgical procedure to be performed, and the opening in the distal end of the outer tubular member has a configuration to cooperate with the particular configuration of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to herein generically as "cutting blades or edges". Cut tissue is aspirated through the hollow lumen of the inner tubular member to be collected via a tube communicating with the handpiece.

It is very important in such surgical cutting instruments that the cutting edge be precisely positioned and aligned relative to the opening in the distal end of the outer tubular member; and, accordingly, a bearing structure must be provided to provide precise positioning and alignment of the cutting edge while permitting unrestricted rotation of the inner tubular member within the outer tubular member. That is, the inner tubular member cannot be allowed to cock or be positioned askew of the longitudinal axis of the surgical cutting instrument as a reaction to the cutting action. This problem has been difficult to overcome in the past. The addition of bearing surfaces at the distal end of the surgical cutting instrument or at spaced positions along the surgical cutting instrument requires complex structure Titanium nitride (TiN) has been used o cutting tools for industrial applications to provide the benefits of longer life and higher productivity as described, for example, in various literature and brochures from Balzers Tool Coatings, Inc. TiN coatings are applied by placing physically and chemically clean tools in fixtures to become the cathode of a high voltage circuit in a reaction chamber that is evacuated and charged with argon. By sputter cleaning, positive argon ions are propelled by a high voltage field and blast the tool to make the tool atomically clean. An electron beam gun heats titanium until the titanium evaporates. Nitrogen is introduced into the chamber, and the titanium ions are electrically accelerated toward the tools. The titanium ion bombardment combines with the nitrogen gas to form a coating of TiN about 0.0001 inch thick on the surface of the tool. The coating process is called "physical vapor deposition" and operates at temperatures in the 900° F. range. In the past, cutting tools have been coated at the cutting edges thereof with TiN by physical vapor deposition for the purpose of hardening the cutting edge thereby providing the cutting tool with an extended useful life; however, there has been no recognition of the use of TiN coatings by physical vapor deposition to limit heat conduction along a rotating tubular member to produce a bearing structure for inner and outer members made of stainless steel.

SUMMARY OF THE INVENTION

Accordingly, it is a primary object of the present invention to overcome the above mentioned problems and disadvantages associated with surgical cutting instruments formed of relatively movable, elongate, inner and outer tubular members.

Another object of the present invention is to provide an elongate bearing structure for a surgical cutting instrument having elongate inner and outer tubular members to prevent cocking or skewing of the inner member relative to the outer member without creating galling and possible seizure during operation of the surgical cutting instrument.

A further object of the present invention is to disperse or distribute heat along the length of a surgical cutting instrument during operation to avoid hot spots and prevent concentration of heat at the cutting edge at the distal end of the surgical cutting instrument.

The present invention has another object in that stainless steel inner and outer tubular members can be used in an elongate surgical cutting instrument without galling or seizure.

Some of the advantages of the present invention over the prior art are that the surgical cutting instrument of the present invention can be economically manufactured for single patient use since precise bearing support is provided without expensive and complex structure modifications and, further, without subjecting the surgical cutting instrument to galling or seizure during operation and the surgical cutting instrument can be manufactured with only a single added process step.

The present invention is generally characterized in a surgical cutting instrument having an elongate outer tubular member having a proximal end, a distal end and an opening disposed at the distal end, an elongate inner tubular member having a proximal end, a distal end and a cutting edge disposed at the distal end, the inner tubular member being movably received in the outer tubular member to position the proximal end of the inner tubular member adjacent the proximal end of the outer tubular member, the distal end of the inner tubular member adjacent the distal end of the outer tubular member and the cutting edge adjacent the opening to permit the cutting edge to engage bodily tissue through the opening, and a coating of titanium nitride formed on the inner tubular member by physical vapor deposition and extending from the distal end to the proximal end of the inner tubular member, the inner tubular member having an outer diameter substantially the same as the inner diameter of the outer tubular member such that the titanium nitride coating forms an elongate bearing surface extending along the length of the surgical cutting instrument.

Other objects and advantages of the present invention will become apparent from the following description of the preferred embodiment taken in conjunction with the accompanying drawings.

DESCRIPTION OF THE PREFERRED EMBODIMENT

Figure 1:
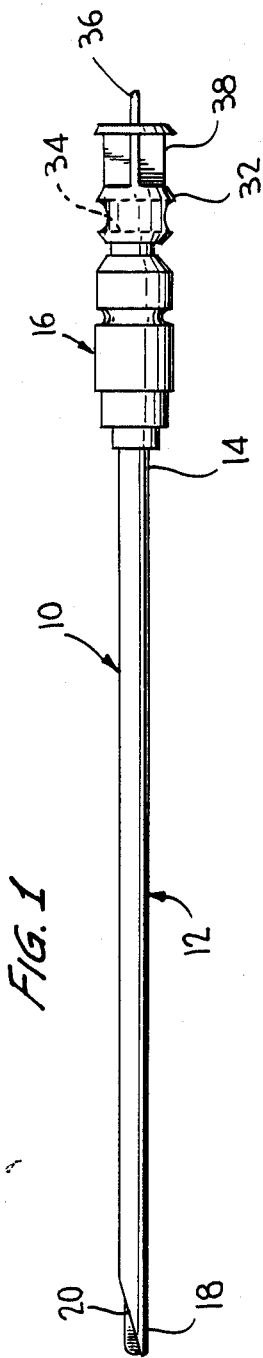
FIG. 1 is a side elevation of a surgical cutting instrument according to the present invention.
Figure 2:
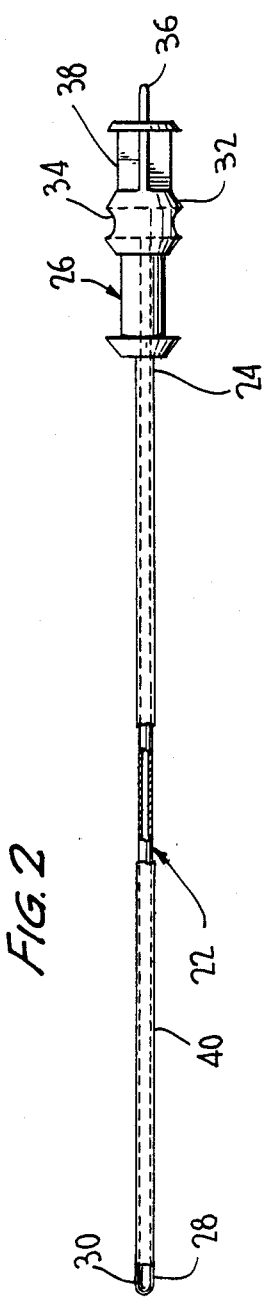
FIG. 2 is a side elevation, partially broken away, of an inner tubular member of the surgical cutting instrument of FIG. 1.
Figure 4:
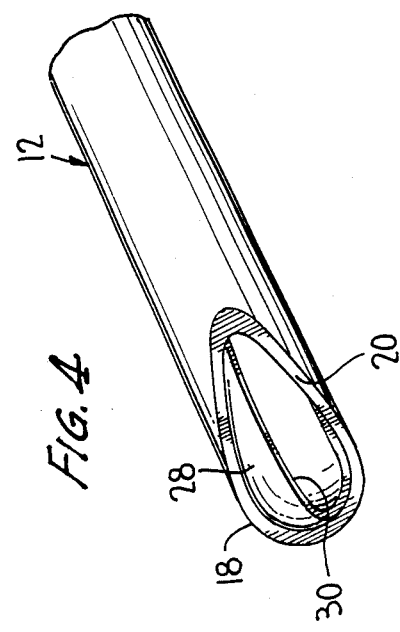
FIG. 4 is an enlarged perspective of the distal end of the surgical cutting instrument of the present invention.

A surgical cutting instrument 10 according to the present invention is illustrated in FIG. 1 and includes an elongate tubular outer member 12 made of stainless steel and having a proximal end 14 fixed to a plastic hub 16 and a distal end 18 having an opening 20 therein forming a cutting port or window. An elongate tubular inner member 22 made of stainless steel is rotatably received in outer tubular member 12 and, as shown in FIG. 2, has a proximal end 24 fixed to a plastic hub 26 having a configuration to be received in a recess (not shown) in hub 16 and a distal end 28 having a cutting edge 30 formed thereon and positioned adjacent opening 20 such that the cutting edge can engage bodily tissue. The hub 26 has a central portion 32 with a transversely extending passage 34 therethrough, the inner tubular member extending through an axial bore in hub 26 to communicate with passage 34. A driven tang 36 extends from a portion 38 formed of transverse ribs and is adapted to be driven by a rotating slotted drive shaft of an electric motor in a handpiece. The structure of hubs 16 and 26 is described in brief general terms only since the hubs are the same as utilized on the INTRA ARC cutting blades manufactured by Concept Incorporated an designed for use with the INTRA ARC Model 9930 arthroscopic drive system of Concept Incorporated and the Model 9950H handpiece thereof. The opening 20 in the distal end of the outer tubular member 12 extends through the side and end walls to produce an edge cooperating with the cutting edge 30 formed on the distal end 28 of the inner tubular member 22 to form a full radius resector. The opening 20 can have any desired configuration to cooperate with the configuration of the cutting edge or edges on the distal end of the inner tubular member including, but not limited to, the various cutting tip designs of the Concept INTRA ARC Blade System, such as to form trimmers, meniscus cutters, end cutters, side cutters, full radius resectors, synovial resectors, whiskers, open end cutters, arthroplasty burrs, slotted whiskers, tapered burrs, oval burrs and punch forceps. While the surgical cutting instrument of the present invention is shown and described for use in the Concept INTRA ARC system, it will be appreciated that the surgical cutting instrument of the present invention can have any desirable hub configuration to be utilized with any drive system or handpiece capable of rotating or reciprocating an elongate inner tubular member within an elongate outer tubular member to cut or otherwise engage bodily tissue at the distal end and aspirate cut tissue through the lumen of the inner tubular member.

Figure 3:
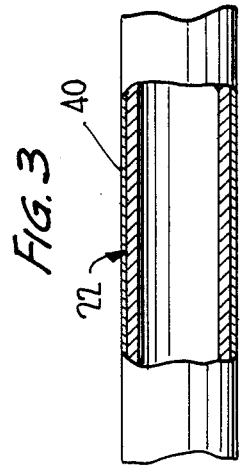
FIG. 3 is an enlarged broken section of the inner tubular member.

In accordance with the present invention, the inner tubular member 22 has a titanium nitride (TiN) coating 40 formed thereon by physical vapor deposition, the coating 40 being disposed along substantially the full length of the inner tubular member from the distal end 28, including the cutting edge 30, to the proximal end 24. It is preferable to coat the entire length of the inner tubular member such that the coating 40 extends under the distal end of the hub 26. The coating of TiN 40 has a thickness of only 0.0001 inch such that the outer diameter of inner tubular member 22 can be substantially the same as the inner diameter of outer tubular member 12 with the coating engaging the inner surface of the outer tubular member to form a bearing along the length of the surgical cutting instrument. By using the TiN coating to form a bearing along the length of the inner tubular member, rather than only on the distal end and cutting edges which engage the bodily tissue, unexpectedly a surgical cutting instrument is provided in an economically feasible manner for single patient use (disposable) while still providing precision positioning of the inner tubular member within the outer tubular member and while using stainless steel inner and outer tubular members. The TiN coating 40 is shown of exaggerated thickness in FIGS. 2 and 3 since the coating is so thin that it cannot be illustrated if the figures are to scale.

In operation, the inner tubular member is rotatable driven in the outer tubular member such that the cutting edge 30 engages bodily tissue via the cutting port or window formed by opening 20, and the cut tissue is aspirated through the lumen of the inner tubular member to exit the surgical cutting instrument via passage 34 which communicates with a suction passage at the handpiece. The cutting edge 30 will be maintained in precise position at the opening 20 due to the bearing formed by the TiN coating along the length of the surgical cutting instrument, and the considerable thrust and radial loads placed on the inner and outer tubular members will not cause galling due to the distribution of heat along the length of the bearing surface created by the TiN coating. In this manner, hot spots are avoided, and the heat distribution or dispersion along the length of the surgical cutting instrument prohibits concentration of heat at the cutting tip as would occur with no coating or coating only at the cutting tip. Accordingly, easier and smoother cutting is accomplished with the surgical cutting instrument of the present invention.

Inasmuch as the present invention is subject to many variations, modifications and changes in detail, it is intended that the subject matter discussed above and shown in the accompanying drawings be interpreted as illustrative and not in a limiting sense.

What is claimed is:

1. A surgical cutting instrument comprising
an elongate outer tubular member having a proximal end, a distal end and an opening disposed at said distal end;
an elongate inner tubular member having a proximal end, a distal end and a cutting edge disposed at said distal end, said inner tubular member being movably received in said outer tubular member to position said proximal end of said inner tubular member adjacent said proximal end of said outer tubular member, said distal end of said inner tubular member adjacent said distal end of said outer tubular member and said cutting edge adjacent said opening to permit said cutting edge to engage bodily tissue through said opening; and
a coating of titanium nitride formed on said inner tubular member by physical vapor deposition and extending from said distal end to said proximal end of said inner tubular member, said inner tubular member having an outer diameter substantially the same as the inner diameter of said outer tubular member such that said titanium nitride coating forms an elongate bearing surface extending along the length of said surgical cutting instrument.

2. A surgical cutting instrument as recited in claim 1 wherein said titanium nitride coating has a thickness of substantially 0.0001 inch.

3. A surgical cutting instrument as recited in claim 2 wherein said outer tubular member and said inner tubular member are each made of stainless steel.

4. A surgical cutting instrument as recited in claim 3 wherein said outer tubular member includes a plastic hub fixed to said proximal end of said outer tubular member and said inner tubular member includes a plastic hub fixed to said proximal end of said inner tubular member and having a portion received in said hub of said outer tubular member and a portion having a passage extending therethrough in communication with the lumen of said inner tubular member for aspiration of cut bodily tissue.

5. A surgical cutting instrument as recited in claim 1 wherein said inner tubular member is rotatably received in said outer tubular member.

6. A surgical cutting instrument as recited in claim 5 wherein said outer tubular member and said inner tubular member are each made of stainless steel and said outer tubular member includes a plastic hub fixed to said proximal end of said outer tubular member and said inner tubular member includes a plastic hub fixed to said proximal end of said inner tubular member over said coating and having a portion received in said hub of said outer tubular member and a portion having a passage extending therethrough in communication with the lumen of said inner tubular member for aspiration of cut bodily tissue.

* * * * *